(12) United States Patent
Jaroch et al.

(10) Patent No.: US 7,067,667 B2
(45) Date of Patent: Jun. 27, 2006

(54) AMINOALKYL-3, 4-DIHYDROQUINOLINE DERIVATIVES AS NO-SYNTHASE INHIBITORS

(75) Inventors: Stefan Jaroch, Berlin (DE); Hartmut Rehwinkel, Berlin (DE); Peter Holscher, Berlin (DE); Detlev Sülzle, Berlin (DE); Margrit Hillmann, Berlin (DE); Gerardine Anne Burton, Berlin (DE); Fiona Mcdougall McDonald, Berlin (DE)

(73) Assignee: Schering Aktiengesellschaft, Berlin (DE)

( * ) Notice: Subject to any disclaimer, the term of this patent is extended or adjusted under 35 U.S.C. 154(b) by 274 days.

(21) Appl. No.: 10/694,845

(22) Filed: Oct. 29, 2003

(65) Prior Publication Data

US 2004/0127712 A1    Jul. 1, 2004

Related U.S. Application Data

(63) Continuation of application No. 09/787,848, filed as application No. PCT/EP99/07091 on Sep. 20, 1999, now abandoned.

(30) Foreign Application Priority Data

Sep. 24, 1998  (DE) ................................ 198 45 830

(51) Int. Cl.
    *C07D 221/12*    (2006.01)
    *A61K 31/44*     (2006.01)
(52) U.S. Cl. ........................ 546/108; 546/109; 514/290
(58) Field of Classification Search ................ 514/290; 546/108, 109
    See application file for complete search history.

(56) References Cited

FOREIGN PATENT DOCUMENTS

DE    3305329    *  8/1984
IN     153442    *  7/1984

OTHER PUBLICATIONS

Hollingsworth, CA 54:62618, abstract of J of Chemical Society, Abstracts, 1960, pp. 263-266.*
Bose, CA 76:85668, abstract only, 1971.*
Keene, CA 63:24038, 1965.s.*
Baberkina, CA 113:78196, 1990.*
Hollingsworth, CA 43:8385, 1948.*

* cited by examiner

*Primary Examiner*—D. Margaret Seaman
(74) *Attorney, Agent, or Firm*—Berlex, Inc.

(57) ABSTRACT

3,4-dihydroquinoline derivatives, a process for their production and their use in pharmaceutical agents.

10 Claims, No Drawings

AMINOALKYL-3, 4-DIHYDROQUINOLINE DERIVATIVES AS NO-SYNTHASE INHIBITORS

This application is a Con of Ser. No. 09/787,848, filed Mar. 23, 2001, now abandoned, which is a 371 of PCT/EP99/07091, filed Sep. 20, 1999, which claims priority to GERMANY 198 45 830.4, filed Sep. 24, 1998.

The invention relates to 3,4-dihydroquinoline derivatives, a process for their production and their use in pharmaceutical agents.

In human cells, there exist at least three forms of nitrogen monoxide syntheses, which convert arginine into nitrogen monoxide (NO) and citrulline. Two constitutive NO-synthases (NOS) were identified that are present as calcium/calmodulin-dependent enzymes in the brain (ncNOS or NOS 1) or in the endothelium (ecNOS or NOS 3). Another isoform is the inducible NOS (iNOS or NOS 2), which is a virtually $Ca^{++}$-independent enzyme and is induced after activation of different cells by endotoxin or other substances.

NOS-inhibitors and especially selective inhibitors of NOS 1, NOS 2 or NOS 3 are therefore suitable for treatment of different diseases, which are induced or aggravated by pathological concentrations of NO in cells.

A number of reviews provide information on the action and inhibitors of NO-synthases. For example, Drugs 1998. 1, 321 or Current Pharmac. Design 1997, 3, 447 can be mentioned.

As NOS-inhibitors, different compounds are known. For example, arginine derivatives, aminopyridines, cyclic amidine derivatives, phenylimidazoles and others are described.

It has now been found that the heterocycles that are substituted according to the invention can be used especially advantageously as pharmaceutical agents.

The invention relates to the compounds of formula I, their tautomeric and isomeric forms and salts

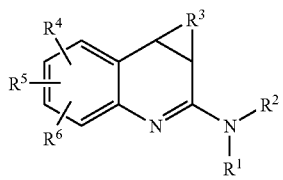

(I)

in which the substituents have the following meaning:
$R^1$ and $R^2$ mean, independently of one another:
a) Hydrogen,
b) $C_{1-6}$ alkyl,
c) $OR^7$,
d) $NR^7R^8$,
e) CN,
f) acyl,
g) $CO_2R^9$,
h) $CONR^7R^8$,
i) $CSNR^7R^8$,
$R^3$ means:
a saturated or unsaturated $C_{1-5}$ alkylene radical, which can be substituted in 1 to 4 places with $OR^7$, $NR^{11}R^{12}$ or $C_{1-4}$ alkyl and in which 1 or 2 $CH_2$ groups can be replaced by O, $S(O)_n$, $NR^8$, $=N-$ or carbonyl, and which can be bridged with a methano, ethano or propano group,
$R^4$ means:
$C_{1-4}$ alkyl, substituted with $NR^{14}R^{15}$ or $R^4$ and $R^5$ together with 2 adjacent carbon atoms form a five- or six-membered carbocyclic compound, which can be substituted with $NR^{14}R^{15}$,
$R^5$ and $R^6$ mean, independently of one another:
a) Hydrogen,
b) halogen,
c) $OR^7$,
d) $C_{1-4}$ alkyl
e) $CF_3$,
f) $OCF_3$,
$R^7$, $R^{18}$ and $R^{19}$ mean, independently of one another:
a) Hydrogen,
b) $C_{1-6}$ alkyl,
c) C6–10-aryl, which optionally is substituted with halogen or $C_{1-4}$ alkyl,
$R^8$, $R^{11}$ and $R^{12}$ mean, independently of one another:
a) Hydrogen,
b) $C_{1-6}$ alkyl,
c) $C_{6-10}$ aryl, which optionally is substituted with halogen or $C_{1-4}$ alkyl,
d) $COR^{10}$,
e) $CO_2R^{10}$,
f) $CONR^{18}R^{19}$,
g) $CSNR^{18}R^{19}$,
$R^9$, $R^{10}$, and $R^{20}$ mean, independently of one another:
a) $C_{1-6}$ alkyl,
b) $C_{6-10}$ aryl, which optionally is substituted with halogen or $C_{1-4}$ alkyl,
$R^{14}$ and $R^{15}$ mean, independently of one another:
a) Hydrogen,
b) $CO_2R^{20}$
c) $C_{1-6}$ alkyl, which optionally is substituted with halogen, hydroxy, $C_{1-4}$ alkoxy, nitro, amino, $C_{1-6}$ alkyl, trifluoromethyl, carboxyl, cyano, carboxamido, $C_{3-7}$ cycloalkyl, indanyl, 1,2,3,4-tetrahydronaphthyl, $C_{6-10}$ aryl, 5- or 6-membered heteroaryl with 1–4 nitrogen, oxygen or sulfur atoms, which can be annelated with benzene, whereby the aryl radical and the heteroaryl radical can be substituted with halogen, hydroxy, $C_{1-4}$ alkoxy, $C_{1-4}$ alkyl, $CF_3$, $NO_2$ $NH_2$, $N(C_{1-4}$ alkyl$)_2$ or carboxyl, or
$R^{14}$ and $R^{15}$ together with the nitrogen atom form a 5- to 7-membered saturated heterocycle, which can contain another oxygen, nitrogen or sulfur atom and can be substituted with $C_{1-4}$ alkyl or a phenyl, benzyl or benzoyl radical that is optionally substituted with halogen, or an unsaturated 5-membered heterocycle, which can contain 1–3 N atoms and can be substituted with phenyl, $C_{1-4}$ alkyl, halogen or $CH_2$—OH, and
n means 0, 1 or 2.

The compounds of the formula can be present as tautomers, stereoisomers or geometric isomers. The invention also comprises all possible isomers, such as E- and Z-isomers, S- and R-enantiomers, cis- and trans-diastereomers, racemates and mixtures thereof, including the tautomeric compounds of Formulas Ia and Ib (for $R^2$=hydrogen).

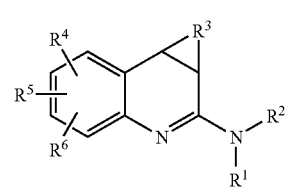

(Ia)

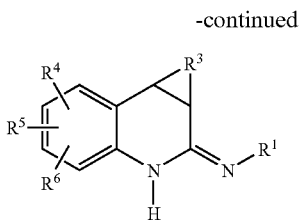

(Ib)

The physiologically compatible salts can be formed with inorganic and organic acids, such as, for example, oxalic acid, lactic acid, citric acid, fumaric acid, acetic acid, maleic acid, tartaric acid, phosphoric acid, hydrochloric acid, hydrobromic acid, sulfuric acid, p-toluenesulfonic acid, methanesulfonic acid, i.a.

For salt formation of acid groups, the inorganic or organic bases are also suitable, which are known for the formation of physiologically compatible salts, such as, for example, alkali hydroxides, such as sodium and potassium hydroxide, alkaline-earth hydroxides, such as calcium hydroxide, ammonia, amines such as ethanolamine, diethanolamine, triethanolamine, N-methylglucamine, tris-(hydroxymethyl)-methylamine, etc.

In each case, alkyl means a straight-chain or branched alkyl group, such as, e.g., methyl, ethyl, propyl, isopropyl, n-butyl, sec-butyl, tert-butyl, n-pentyl, sec-pentyl, tert-pentyl, neopentyl, n-hexyl, sec-hexyl, heptyl, or octyl.

Cycloalkyl is defined respectively as cyclopropyl, cyclobutyl, cyclopentyl, cyclohexyl or cycloheptyl.

As a bicyclic compound $R^3$, for example, bicyclo[2.2.1] heptane, bicyclo[2.2.2]octane and bicyclo[3.2.1]octane can be considered.

Halogen means respectively fluorine, chlorine, bromine or iodine.

Aryl is defined respectively as naphthyl or especially phenyl, which can be substituted by the same or a different component in any position in one to three places.

In each case, the hetaryl radical can contain a slightly condensed benzene ring and can be substituted by the same or a different component in one to three places. For example, the following 5- and 6-ring heteroaromatic compounds are suitable:

Imidazole, indole, isooxazole, isothiazole, furan, oxadiazole, oxazole, pyrazine, pyridazine, pyrimidine, pyridine, pyrazole, pyrrole, tetrazole, thiazole, triazole, thiophene, thiadiazole, benzimidazole, benzofuran, benzoxazole, isoquinoline, quinoline. Preferred are 5- and 6-membered heteroaromatic compounds with 1 to 2 nitrogen, oxygen or sulfur atoms and especially furanyl and thienyl. As substituents of the heteroaryl radical, especially $NO_2$, CN, halogen, $C_{1-4}$ alkyl and $CF_3$ are suitable.

As a saturated heterocycle $NR^{14}R^{15}$, for example, piperidine, pyrrolidine, morpholine, thiomorpholine, hexahydroazepine and piperazine can be mentioned. The heterocycle can be substituted in 1 to 3 places with $C_{1-4}$ alkyl or a phenyl, benzyl or benzoyl radical that is optionally substituted with halogen. For example, there can be mentioned: N-methyl-piperazine, 2,6-dimethylmorpholine, phenylpiperazine or 4-(4-fluorobenzoyl)-piperidine.

If $NR^{14}R^{15}$ together with the nitrogen atom form an unsaturated heterocycle, for example, imidazole, pyrrole, pyrazole, triazole, benzimidazole and indazole can be mentioned, which can be substituted in one to two places with phenyl, $C_{1-4}$ alkyl, halogen, especially chlorine or $CH_2$—OH.

If $R^{14}$ or $R^{15}$ means indanyl or 1,2,3,4-tetrahydronaphthyl, this radical can be linked in each case in 1- or 2-position.

If $R^4$ and $R^5$ together with two adjacent carbon atoms form a carbocyclic compound, the latter can be in any position and can be substituted in any position in one or two places with $NR^{14}R^{15}$. Simple substitution is preferred. $R^4$ and $R^5$ preferably mean $C_3$–$C_4$ alkylene.

The acyl radical is derived from straight-chain or branched aliphatic $C_{1-6}$ carboxylic acids, such as, for example, formic acid, acetic acid, propionic acid, butyric acid, trimethylacetic acid or caproic acid or from known benzenesulfonic acids, which can be substituted with halogen or $C_{1-4}$ alkyl, and $C_{1-4}$ alkanesulfonic acids, such as methanesulfonic acid, and p-toluenesulfonic acid. Preferably alkanoyls can be mentioned.

The preferred embodiment of $R^1$ and $R^2$ is hydrogen.

$R^3$ preferably means alkylene with 1–5 carbon atoms, in which 1 or 2 $CH_2$ groups can be replaced by O or S and especially $C_{1-5}$ alkylene.

$R^5$ in particular means hydrogen or together with $R^4$ and with two adjacent carbon atoms forms a 5- or 6-membered carbocyclic compound, which is substituted with $NR^4R^{15}$.

Preferred embodiments for $R^6$ are hydrogen and halogen and for $R^{14}$ hydrogen and $CO_2R^{20}$.

The invention also relates to the use of the compounds according to the invention for the production of a pharmaceutical agent for treating diseases, which are induced by the action of nitrogen monoxide at pathological concentrations. These include neurodegenerative diseases, inflammatory diseases, auto-immune diseases, and cardiovascular diseases.

For example, there can be mentioned:

Cerebral ischemia, hypoxia and other neurodegenerative diseases, which are brought into contact with inflammations, such as multiple sclerosis, amyotrophic lateral sclerosis and comparable sclerotic diseases, Parkinson's Disease, Huntington's Disease, Korksakoff's Disease, epilepsy, vomiting, stress, sleep disorders, schizophrenia, depression, migraine, pain, hypoglycemia, dementia, such as, e.g., Alzheimer's Disease, HIV-dementia and presenile dementia.

They are also suitable for treating diseases of the cardiovascular system and for treating auto-immune and/or inflammatory diseases, such as hypotension, ARDS (adult respiratory distress syndrome), sepsis or septic shock, rheumatoid arthritis, osteoarthritis, insulin-dependent diabetes mellitus (IDDM), inflammatory disease of the pelvis/intestine (bowel disease), meningitis, glomerulonephritis, acute and chronic liver diseases, diseases by rejection (for example allogenic heart, kidney or liver transplants) or inflammatory skin diseases such as psoriasis, etc.

Based on their profile of action, the compounds according to the invention are very well suited for inhibiting the neuronal NOS.

To use the compounds according to the invention as pharmaceutical agents, they are brought into the form of a pharmaceutical preparation, which in addition to the active ingredient contains vehicles, adjuvants and/or additives that are suitable for enteral or parenteral administration. The administration can be done orally or sublingually as a solid in the form of capsules or tablets or as a liquid in the form of solutions, suspensions, elixirs, aerosols or emulsions or rectally in the form of suppositories or in the form of injection solutions that can also optionally be administered subcutaneously, intramuscularly or intravenously, or topically in the form of transdermal systems and aerosols or intrathecally. As adjuvants for the desired pharmaceutical agent formulation, the inert organic and inorganic support media that are known to one skilled in the art are suitable, such as, e.g., water, gelatin, gum arabic, lactose, starch, magnesium stearate, talc, plant oils, polyalkylene glycols, etc. Moreover, preservatives, stabilizers, wetting agents, emulsifiers or salts for changing the osmotic pressure or buffers can optionally be contained.

For parenteral administration, especially injection solutions or suspensions, especially aqueous solutions of the active compounds in polyhydroxyethylated castor oil, are suitable.

As vehicle systems, surface-active adjuvants such as salts of bile acids or animal or plant phospholipids, but also mixtures thereof as well as liposomes or their components can be used.

For oral administration, especially tablets, coated tablets or capsules with talc and/or hydrocarbon vehicles or binders, such as, for example, lactose, corn or potato starch, are suitable. The administration can also be done in liquid form, such as, for example, as a juice, to which optionally a sweetener is added.

The dosage of the active ingredient can vary depending on method of administration, age and weight of the patient, type and severity of the disease that is to be treated and similar factors. The daily dose is 1–2000 mg, preferably 20–500 mg, whereby the dose can be given as an individual dose to be administered one time or divided into 2 or more daily doses.

The NOS-inhibitory action of the compounds of Formula (I) and their physiologically compatible salts can be determined according to the methods by Bredt and Snyder in Proc. Natl. Acad. Sci. USA (1989) 86, 9030–9033. The bNOS inhibition of Example 8 (4-amino-8-chloro-7-(3-chlorobenzylamino)-ethyl-2,3,3a,9b-tetrahydro-1H-cyclopenta[c]quinoline dihydrochloride) is $IC_{50}$=190 nM.

The production of the compounds according to the invention is carried out in that a compound of formula (II) or its salt

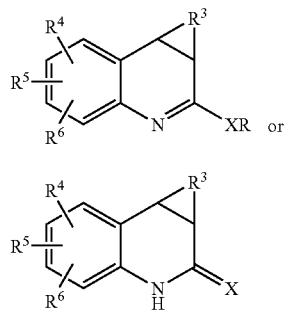

in which $R^3$ to $R^6$ has the above meaning, R means methyl or ethyl and X=O or S, is reacted with ammonia, primary or secondary amines, hydroxylamine and its derivatives or hydrazine and its derivatives, and optionally then the isomers are separated or the salts are formed.

The reaction with ammonia is possible under pressure in autoclaves with excess ammonia at low temperatures (–78° C.) or by stirring in methanol that is saturated with ammonia. Thiolactams are preferably reacted. If the reaction is with amines, first the iminoethers or iminothioethers are produced from lactam or thiolactam as intermediate compounds (e.g., with methyl iodide or dimethyl sulfate), and the latter are reacted with or without isolation with the corresponding amines or their salts.

The isomer mixtures can be separated into enantiomers or E/Z-isomers according to commonly used methods, such as, for example, crystallization, chromatography or salt formation. The enantiomers can also be obtained by chromatography on chiral phases as well as by stereoselective syntheses.

The production of the salts is carried out in the usual way, by a solution of the compound of Formula (I) being mixed with the equivalent amount of acid or excess acid, which optionally is in solution, and the precipitate being separated or the solution being worked up in the usual way.

If the production of the starting compounds is not described, the latter are known and commercially available or can be produced analogously to known compounds or according to processes that are described here.

In the precursor stages, optionally sulfides are oxidized, esters are saponified, acids are esterified, hydroxyl groups are etherified or acylated, amines are acylated, alkylated, diazotized, halogenated, $NO_2$ is introduced or reduced, reacted with isocyanates or isothiocyanates, the isomers are separated or the salts are formed.

In addition, a nitro group or halogen, especially chlorine and bromine, can be introduced by electrophilic, aromatic substitution. Mixtures that are produced in this case can be separated in the usual way, also using HPLC. If a nitrile is present, the latter can be saponified according to known processes or can be introduced into the corresponding amine, tetrazole or amidoxime.

The reduction of the nitro group or optionally the cyano group to the amino group is carried out catalytically in polar solvents at room temperature or at an elevated temperature under hydrogen pressure. As catalysts, metals such as Raney nickel or noble metal catalysts such as palladium or platinum optionally in the presence of barium sulfate or on vehicles are suitable. Instead of hydrogen, ammonium formate or formic acid can also be used in a known way. Reducing agents such as tin(II) chloride or titanium(III) chloride can also be used, such as complex metal hydrides, optionally in the presence of heavy metal salts. For nitro groups, reduction with zinc in water-ethanol-THF/ammonium chloride or iron in acetic acid has proven its value.

If a single or multiple alkylation of an amino group or a CH-acid carbon position is desired, alkylation can be performed with, for example, alkyl halides according to commonly used methods. Protection of the lactam group as an anion by a second equivalent base or by a suitable protective group optionally is necessary.

The acylation of the amino group is carried out in the usual way with, for example, an acid halide or acid anhydride, optionally in the presence of a base.

The introduction of the halogens chlorine, bromine or iodine via the amino group can also be carried out, for example, according to Sandmeyer, by the diazonium salts that are formed intermediately with nitrites being reacted with Cu(I) chloride or Cu(I) bromide in the presence of the corresponding acids such as hydrochloric acid or hydrobromic acid or being reacted with potassium iodide.

The introduction of an $NO_2$ group is possible by a number of known nitration methods. For example, nitration can be performed with nitrates or with nitronium tetrafluoroborate in inert solvents, such as halogenated hydrocarbons or in sulfolane or glacial acetic acid. Introduction by, e.g., nitrating acid in water, acetic acid or concentrated sulfur acid as a solvent is also possible at temperatures of between –10° C. and 30° C.

Thiolactams of formula (IIb, X=S) are obtained, for example, from lactams with phosphorus pentasulfide ($P_4S_{10}$)

or 2,4-bis(4-methoxyphenyl)-1,3,2,4-dithiaphosphetane-2,4-disulfide (Lawesson's reagent) in suitable solvents. Compounds of Formula (IIa) can be obtained by, for example, reaction with Meerwein reagent (trimethyloxonium tetrafluoroborate).

The invention also relates to the compounds of formula IIb

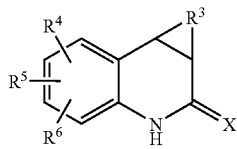

(IIb)

in which $R^3$ to $R^6$ have the above meaning, and X=O or S, which produce intermediate compounds in the production of pharmacologically active compounds and are obtained and further processed according to the described process.

The production of the compounds of Formula (IIb, X=O) is done in the way that is known to one skilled in the art. It can be done, for example, in that a compound of Formula (III)

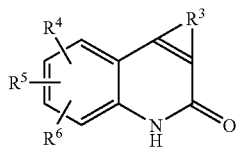

(III)

is reduced to lactam (II) with an alkali or alkaline-earth metal or an amalgam of the same in alcohol (cf. B. K. Blount, W. H. Perkin, S. G. P. Plant, J. Chem. Soc. 1929, 1975; R. Brettle, S. M. Shibib, J. Chem. Soc. Perkin Trans 1, 1981, 2912).

The production of quinolines of type (III) is carried out in the way that is known to one skilled in the art, e.g., according to B. K. Blount, W. H. Perkin, S. G. P. Plant, J. Chem. Soc. 1929, 1975; W. Ried, W. Käppeler, Liebigs Ann. Chem. 1965, 688, 177; L. A. White, R. C. Storr, Tetrahedron 1996, 52, 3117.

The introduction of substituents $R^4$–$R^6$ can also be carried out in the stage of compound (III) and takes place as described above.

For example, the production of compounds of Formula II with $R^4$ in the meaning of an alkyl radical that is substituted with $NR^{14}R^{15}$ by reductive amination of the corresponding aldehyde or if $R^4$ and $R^5$ form a 5- or 6-membered carbocyclic compound, which is substituted with $NR^{14}R^{15}$, can be carried out by reductive amination of the corresponding ketone. If the introduction of a heteroaryl radical $NR^{14}R^{15}$ is desired, the corresponding halogen derivative can be substituted nucleophilically. If a primary or secondary amino group is present, it may be advantageous to protect the latter intermediately, for example by introduction of a tert-butoxycarbonyl group, which is usually cleaved according to the amidine formation.

New compounds were identified by one or more of the following methods: melting point, mass spectroscopy, infrared spectroscopy, nuclear magnetic resonance spectroscopy (NMR). NMR spectra were measured with a Bruker 300 MHz device; the (deuterated) solvents were respectively indicated and abbreviated as follows: $CDCl_3$ (chloroform), $CD_3OD$ ([$D_4$]-methanol), DMSO ([$D_6$]-dimethyl sulfoxide). Alterations are indicated in delta and ppm. Here: m means multiplet, several signals; s means singlet; d means doublet; dd means double doublet, etc.; t means triplet; q means quartet; H means hydrogen protons. In addition, THF means tetrahydrofuran, DMF means N,N-dimethylformamide, MeOH means methanol, and ml means milliliter. All solvents are p.A. equivalent base or by a suitable protective group optionally is necessary.

The acylation of the amino group is carried out in the usual way with, for example, an acid halide or acid anhydride, optionally in the presence of a base.

The introduction of the halogens chlorine, bromine or iodine via the amino group can also be carried out, for example, according to Sandmeyer, by the diazonium salts that are formed intermediately with nitrites being reacted with Cu(I) chloride or Cu(I) bromide in the presence of the corresponding acids such as hydrochloric acid or hydrobromic acid or being reacted with potassium iodide.

The introduction of an $NO_2$ group is possible by a number of known nitration methods. For example, nitration can be performed with nitrates or with nitronium tetrafluoroborate in inert solvents, such as halogenated hydrocarbons or in sulfolane or glacial acetic acid. Introduction by, e.g., nitrating acid in water, acetic acid or concentrated sulfur acid as a solvent is also possible at temperatures of between –10° C. and 30° C.

Thiolactams of formula (IIb, X=S) are obtained, for example, from lactams with phosphorus pentasulfide ($P_4S_{10}$) or 2,4-bis(4-methoxyphenyl)-1,3,2,4-dithiaphosphetane-2,4-disulfide (Lawesson's reagent) in suitable solvents. Compounds of Formula (IIa) can be obtained by, for example, reaction with Meerwein reagent (trimethyloxonium tetrafluoroborate).

The invention also relates to the compounds of formula IIb

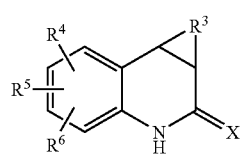

(IIb)

in which $R^3$ to $R^6$ have the above meaning, and X=O or S, which produce intermediate compounds in the production of pharmacologically active compounds and are obtained and further processed according to the described process.

The production of the compounds of Formula (IIb, X=O) is done in the way that is known to one skilled in the art. It can be done, for example, in that a compound of Formula (III)

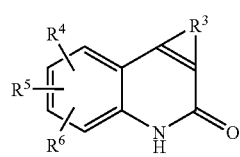

(III)

is reduced to lactam (II) with an alkali or alkaline-earth metal or an amalgam of the same in alcohol (cf. B. K. Blount, W. H. Perkin, S. G. P. Plant, J. Chem. Soc. 1929, 1975; R. Brettle, S. M. Shibib, J. Chem. Soc. Perkin Trans 1, 1981, 2912).

The production of quinolines of type (III) is carried out in the way that is known to one skilled in the art, e.g., according to B. K. Blount, W. H. Perkin, S. G. P. Plant, J. Chem. Soc. 1929, 1975; W. Ried, W. Käppeler, Liebigs Ann. Chem. 1965, 688, 177; L. A. White, R. C. Storr, Tetrahedron 1996, 52, 3117.

The introduction of substituents $R^4$–$R^6$ can also be carried out in the stage of compound (III) and takes place as described above.

For example, the production of compounds of Formula II with $R^4$ in the meaning of an alkyl radical that is substituted with $NR^{14}R^{15}$ by reductive amination of the corresponding aldehyde or if $R^4$ and $R^5$ form a 5- or 6-membered carbocyclic compound, which is substituted with $NR^{14}R^{15}$, can be carried out by reductive amination of the corresponding ketone. If the introduction of a heteroaryl radical $NR^{14}R^{15}$ is desired, the corresponding halogen derivative can be substituted nucleophilically. If a primary or secondary amino group is present, it may be advantageous to protect the latter intermediately, for example by introduction of a tert-butoxycarbonyl group, which is usually cleaved according to the amidine formation.

New compounds were identified by one or more of the following methods: melting point, mass spectroscopy, infrared spectroscopy, nuclear magnetic resonance spectroscopy (NMR). NMR spectra were measured with a Bruker 300 MHz device; the (deuterated) solvents were respectively indicated and abbreviated as follows: $CDCl_3$ (chloroform), $CD_3OD$ ([$D_4$]-methanol), DMSO ([$D_6$]-dimethyl sulfoxide). Alterations are indicated in delta and ppm. Here: m means multiplet, several signals; s means singlet; d means doublet; dd means double doublet, etc.; t means triplet; q means quartet; H means hydrogen protons. In addition, THF means tetrahydrofuran, DMF means N,N-dimethylformamide, MeOH means methanol, and ml means milliliter. All solvents are p.A. grade, unless otherwise indicated. All reactions are performed under protective gas, unless these are aqueous solutions. Melting points are indicated in degrees Celsius and are not corrected.

Below, the production of several precursors, intermediate products and products is described by way of example.

Starting Compounds

7-Bromo-1,2,3,5-tetrahydrocyclopenta[c]quinolin-4-one 15.2 ml (101 mmol) of 1-morpholino-1-cyclopentene is carefully added in drops to a solution of 20.0 g (101 mmol) of 3-bromophenylisocyanate in 100 ml of chloroform. The batch is refluxed for 15 minutes and concentrated by evaporation in a vacuum. Column chromatography on silica gel with hexane-ethyl acetate yielded 25.0 g (88.6 mmol) of cyclopentan-2-one-1-carboxylic acid-(3-bromophenyl) amide. The latter is mixed with 83 ml of concentrated sulfuric acid and stirred for 30 minutes at 90° C. After cooling to room temperature, the batch is poured onto 600 g of ice, the precipitated solid is suctioned off and recrystallized from ethanol: 17.0 g of product.

[1H]-NMR ([$D_6$]DMSO): 2.11 (pent., 2H), 2.74 (t, 2H), 3.07 (t, 2H), 7.34 (dd, 1H), 7.49 (d, 1H), 7.52 (d, 1H), 11.68 (s, 1H).

7-(2-Furanyl)-1,2,3,5-tetrahydrocyclopenta[c]quinolin-4-one

A suspension of 1.32 g (5.0 mmol) of 7-bromo-1,2,3,5-tetrahydrocyclo-penta[c]quinolin-4-one in 200 mL of toluene is mixed with 1.7 ml (5.5 mmol) of 2-(tributyl-stannyl) furan and 0.29 g (0.25 mmol) of tetrakis (triphenylphosphine)palladium. The reaction mixture is degassed, aerated with nitrogen, stirred for 15 hours at room temperature and heated for 4.5 hours to 110° C. The batch is mixed with silica gel and concentrated by evaporation in a vacuum. Column chromatography of the residue on silica gel with hexane-ethyl acetate yields 1.33 g of product.

$^1$H-NMR ([$D_6$]DMSO/$CDCl_3$): 2.00 (pent., 2H), 2.70 (t, 2H), 2.91 (t, 2H), 6.30 (dd, 1H), 6.58 (d, 1H), 7.22-7.31 (m, 3H), 7.44 (d, 1H), 11.09 (br.s, 1H).

7-(2-Furanyl)-1,2,3,3a,5,9b-hexahydrocyclopenta[c]quinolin-4-one

A solution of 1.32 g (5.3 mmol) of 7-(2-furanyl)-1,2,3,5-tetrahydrocyclo-penta[c]quinolin-4-one in 300 ml of methanol is mixed with 2.58 g (10.6 mmol) of magnesium and 0.06 ml of acetic acid. After 15 hours at room temperature, another 1.29 g (5.3 mmol) of magnesium is added to it. The batch is stirred for 15 hours at room temperature, treated with 10% hydrochloric acid (500 ml) and extracted with ethyl acetate (3×300 ml). The combined extracts are dried ($Na_2SO_4$) and concentrated by evaporation in a vacuum. Column chromatography on silica gel with hexane-ethyl acetate yields 0.49 g of product.

$^1$H-NMR ($CDCl_3$): 1.60–1.80 (m, 3H), 2.05–2.20 (m, 2H), 2.34 (m, 1H), 2.98 (td, 1H), 3.26 (q, 1H), 6.48 (dd, 1H), 6.64 (d, 1H), 7.04 (d, 1H), 7.22 (d, 1H), 7.32 (dd, 1H), 7.47 (d, 1H), 8.04 (br.s, 1H).

1,2,3,3a,5,9b-Hexahydrocyclopenta[c]quinolin-4-one-7-carboxylic Acid

A suspension of 0.37 g (1.5 mmol) of 7-(2-furanyl)-1,2,3,3a,5,9b-hexahydro-cyclopenta[c]quinolin-4-one is suspended in 50 ml of acetonitrile-carbon tetrachloride-water (2:1:2) and mixed with 4.81 g (22.5 mmol) of sodium periodate and 40 mg (0.3 mmol) of ruthenium(IV) oxide. After 24 hours at room temperature, the batch is diluted with water (100 ml) and extracted with ethyl acetate (3×100 ml). The combined extracts are dried ($Na_2SO_4$) and concentrated by evaporation in a vacuum. The residue is dissolved in 100 ml of 0.5 M potassium hydroxide solution. The solution is washed with methyl-tert-butyl ether (2×100 ml), acidified with concentrated hydrochloric acid and extracted with ethyl acetate (3×100 ml). The combined extracts are dried ($Na_2SO_4$) and concentrated by evaporation in a vacuum: 213 mg of product.

$^1$H-NMR ([$D_6$]DMSO/$CDCl_3$): 1.38–1.58 (m, 3H), 1.80–1.95 (m, 2H), 2.11 (m, 1H), 2.71 (td, 1H), 3.08 (q, 1H), 7.03 (d, 1H), 7.34 (d, 1H), 7.42 (dd, 1H), 9.35 (s, 1H).

7-Hydroxymethyl-1,2,3,3a,5,9b-hexahydrocyclopenta[c]quinolin-4-one

A solution of 150 mg (0.65 mmol) of 1,2,3,3a,5,9b-hexahydrocyclopenta[c]-quinolin-4-one-7-carboxylic acid in 20 ml of THF is mixed with 0.10 ml (0.70 mmol) of triethylamine and 0.07 ml (0.70 mmol) of ethyl chloroformate at room temperature. After 10 minutes, 76 mg (2.0 mmol) of sodium borohydride is added, and within 20 minutes, 10 ml of methanol is added in drops to it. The batch is stirred for 15 hours at room temperature, diluted with ethyl acetate (100 ml), washed with 20% citric acid (50 ml) and saturated NaCl (50 ml), dried ($Na_2SO_4$) and concentrated by evaporation in a vacuum. Column chromatography on silica gel with hexane-ethyl acetate yields 65 mg of product.

$^1$H-NMR (CDCl$_3$): 1.54–1.79 (m, 3H), 2.02–2.18 (m, 3H), 2.30 (m, 1H), 2.93 (td, 1H), 3.24 (q, 1H), 4.67 (d, 2H), 6.80 (s, 1H), 6.99 (d, 1H), 7.18 (d, 1H), 8.26 (s, 1H).

1,2,3,3a, 5,9b-Hexahydrocyclopenta[c]quinolin-4-one-7-carbaldehyde

A solution of 187 mg (0.86 mmol) of 7-hydroxymethyl-1,2,3,3a,5,9b-hexahydrocyclopenta[c]quinolin-4-one in 20 ml of chloroform-dichloromethane-acetonitrile (2:1:1) is mixed with 151 mg (1.29 mmol) of N-methylmorpholin-N-oxide and 1.5 g of molecular sieve 4 Å. After 15 mg (0.043 mmol) of tetrapropylammonium perruthenate (TPAP) is added, the batch is stirred for 2.5 hours at room temperature, before another 10 mg (0.028 mmol) of TPAP is added. After 1.5 hours, silica gel is added to the reaction mixture, and the solvent is distilled off in a vacuum. Column chromatography with hexane-ethyl acetate yields 156 mg of product.

$^1$H-NMR (CDCl$_3$): 1.60–1.83 (m, 3H), 2.08–2.23 (m, 2H), 2.40 (m, 1H), 3.01 (td, 1H), 3.34 (q, 1H), 7.30 (d, 1H), 7.49 (d, 1H), 7.53 (dd, 1H), 8.63 (br.s, 1H), 9.96 (s, 1H).

7-(3-Chlorobenzylamino)methyl-1,2,3,3a,5,9b-hexahydrocyclopenta[c]quinolin-4-one A solution of 150 mg (0.70 mmol) of 1,2,3,3a,5,9b-hexahydrocyclopenta[c]-quinolin-4-one-7-carbaldehyde in 15 ml of 1,2-dichloroethane is mixed with 0.10 ml (0.84 mmol) and 267 mg (1.26 mmol) of sodium (triacetoxy) borohydride. After 0.04 ml of acetic acid is added, the batch is stirred for 15 hours at room temperature, diluted with ethyl acetate (100 ml), washed with water (20 ml), dried (Na$_2$SO$_4$) and concentrated by evaporation in a vacuum. Column chromatography on silica gel with dichloromethane-ethanol yields 214 mg of product.

$^1$H-NMR (CDCl$_3$): 1.58–1.78 (m, 3H), 2.03–2.19 (m, 2H), 2.31 (m, 1H), 2.95 (td, 1H), 3.26 (q, 1H), 3.75 (s, 2H), 3.80 (s, 2H), 6.75 (dd, 1H), 6.97 (dd, 1H), 7.16 (d, 1H), 7.22-7.32 (m, 3H), 7.37 (s, 1H), 8.41 (br.s, 1H).

7-(N-tert-Butoxycarbonyl-3-chlorobenzylamino)methyl-1,2,3,3a,5,9b-hexahydrocyclopenta[c]quinolin-4-one A solution of 207 mg (0.61 mmol) of 7-(3-chlorobenzylamino)-methyl-1,2,3,3a,5,9b-hexahydrocyclopenta[c]quinolin-4-one in 20 ml of THF is mixed with 201 mg (0.92 mmol) of di-tert-butylcarboxylic acid anhydride and 4 mg (0.03 mmol) of 4-(dimethylamino)pyridine, and it is stirred for 3 hours at room temperature, before another 201 mg (0.92 mmol) of di-tert-butylcarboxylic acid anhydride is added to it.

After 15 hours at room temperature, the batch is diluted with ethyl acetate (100 ml), washed with 20% citric acid (50 ml) and saturated NaCl (20 ml), dried (Na$_2$SO$_4$) and concentrated by evaporation in a vacuum. Column chromatography on silica gel with hexane-ethyl acetate yields 76 mg of product.

$^1$H-NMR (CDCl$_3$): 1.52 (s, 9H), 1.40–1.80 (m, 3H), 2.00–2.20 (m, 2H), 2.34 (m, 1H), 2.95 (td, 1H), 3.26 (q, 1H), 4.32 (br., 2H), 4.40 (br., 2H), 6.55 (br., 1H), 6.85 (br., 1H), 7.08 (br., 1H), 7.13 (d, 1H), 7.21–7.32 (m, 3H), 7.56–7.70 (br., 1H).

MS (FAB) m/e =441 (M$^+$)

104 mg of 5-tert-butoxycarbonyl-7-(N-tert-butoxycarbonyl-3-chlorobenzylamino)methyl-1,2,3,3a,5,9b-hexahydrocyclopenta[c]quinolin-4-one is isolated, moreover.

7-(N-tert-Butoxycarbonyl-3-chlorobenzylamino)methyl-1,2,3,3a,5,9b-hexahydrocyclopenta[c]quinoline-4-thione A solution of 75 mg (0.17 mmol) of 7-(N-tert-butoxycarbonyl-3-chlorobenzyl-amino)methyl-1,2,3,3a,5,9b-hexahydrocyclopenta[c]quinolin-4-one in 5 ml of 1,2-dimethoxyethane is mixed with 138 mg (0.34 mmol) of Lawesson's reagent. After 1.5 hours at room temperature, the batch is refluxed for 0.75 hour and then concentrated by evaporation in a vacuum. Column chromatography on silica gel with hexane-ethyl acetate yields 65 mg of product.

$^1$H-NMR (CDCl$_3$): 1.53 (s, 9H), 1.48–1.78 (m, 2H), 1.93 (m, 1H), 2.10–2.39 (m, 2H), 3.23–3.36 (m, 2H), 4.33 (br., 2H), 4.49 (br., 2H), 6.58 and 6.68 (br., 1H), 6.95 (br.d, 1H), 7.08 (br., 1H), 7.17 (br.s, 1H), 7.21 (d, 1H), 7.24–7.31 (m, 2H), 9.40 (s, 1H).

MS (FAB) m/e=457 (M$^+$)

7-Vinyl-1,2,3,5-tetrahydrocyclopenta[c]quinolin-4-one

A solution of 2.0 g (7.6 mmol) of 7-bromo-1,2,3,5-tetrahydrocyclopenta[c]quinolin-4-one, 2.6 mL (9.9 mmol) of vinyltributyltin and 0.44 g (0.38 mmol) of tetrakis(triphenylphosphine)palladium is degassed and aerated with nitrogen. After six hours of heating to 110° C., the batch is concentrated by evaporation, and the residue is taken up on silica gel. Column chromatography on silica gel with hexane-ethyl acetate yields 1.41 g of product.

$^1$H-NMR (CDCl$_3$): 2.26 (pent., 2H), 3.05 (t, 2H), 3.16 (t, 2H), 5.41 (d, 1H), 5.91 (d, 1H), 6.82 (dd, 1H), 7.33 (d, 1H), 7.38 (s, 1H), 7.49 (d, 1H), 11.22 (br.s, 1H).

7-Oxiranyl-1,2,3,5-tetrahydrocyclopenta[c]quinolin-4-one

A solution of 1.41 g (6.7 mmol) of 7-vinyl-1,2,3,5-tetrahydrocyclopenta[c]-quinolin-4-one in 200 ml of chloroform is mixed at room temperature with mCPBA. After 15 hours at room temperature, the batch is washed with saturated Na$_2$SO$_3$ (2×100 ml), dried (Na$_2$SO$_4$) and concentrated by evaporation in a vacuum. Column chromatography on silica gel with hexane-ethyl acetate yields 0.59 g of product.

$^1$H-NMR (CDCl$_3$): 2.25 (pent., 2H), 2.85 (dd, 1H), 3.03 (t, 2H), 3.13 (t, 2H), 3.20 (dd, 1H), 3.98 (dd, 1H), 7.11 (dd, 1H), 7.35 (d, 1H), 7.49 (d, 1H), 11.44 (br.s, 1H).

7-Hydroxyethyl-1,2,3,3a,5,9b-hexahydrocyclopenta[c]quinolin-4-one

A solution of 0.59 g (2.6 mmol) of 7-oxiranyl-1,2,3,5-tetrahydrocyclopenta[c]-quinolin-4-one in 100 ml of methanol is mixed with 1.26 g (52.0 mmol) of magnesium and 0.06 ml of acetic acid. The batch is stirred for 4 hours at room temperature and mixed with another 0.63 g (26.0 mmol) of magnesium. After 15 hours at room temperature, the reaction mixture is acidified with 200 ml of 10% hydrochloric acid and extracted with ethyl acetate (3×200 ml). The combined extracts are dried (Na$_2$SO$_4$) and concentrated by evaporation in a vacuum. Column chromatography on silica gel with hexane-ethyl acetate yields 0.39 g of product.

$^1$H-NMR (CDCl$_3$): 1.57–1.78 (m, 3H), 2.01–2.18 (m, 2H), 2.29 (m, 1H), 2.82 (t, 2H), 2.93 (td, 1H), 3.23 (q, 1H), 3.86 (t, 2H), 6.62 (d, 1H), 6.88 (dd, 1H), 7.15 (d, 1H), 8.31 (br.s, 1H).

7-(3-Chlorobenzylamino)ethyl-1,2,3,3a,5,9b-hexahydrocyclopenta[c]quinolin-4-one

A solution of 0.19 g (0.82 mmol) of 7-hydroxyethyl-1,2,3,3a,5,9b-hexahydro-cyclopenta[c]quinolin-4-one in 20 ml of dichloromethane is mixed at 0° C. with 0.38 g (0.90 mmol) of 1,1,1-triacetoxy-1,1-dihydro-1,2-benziodoxol-3(1H)-one (D. B. Dess, J. C. Martin, J. Am. Chem. Soc. 1991, 113, 7277). The batch is stirred for 10 minutes at 0° C. and for 40 minutes at room temperature, diluted with dichloromethane (100 ml), washed with saturated NaHCO$_3$ (30 ml), dried (Na$_2$SO$_4$) and concentrated by evaporation in a vacuum. The residue is dissolved in 1,2-dichloroethane (20 ml) and mixed with 0.11 ml (0.90 mmol) of 3-chlorobenzylamine, 0.30 g (1.40 mmol) of sodium (triacetoxy)borohydride and 0.05 ml (0.85 mmol) of acetic acid. After 20 hours at room temperature, the batch is diluted with ethyl acetate (150 ml), washed with water (2×50 ml), dried (Na$_2$SO$_4$) and concentrated by evaporation in a vacuum. Column chromatography on silica gel with dichloromethane-ethanol yields 69 mg of product.

$^1$H-NMR (CDCl$_3$): 1.54–1.77 (m, 3H), 2.01–2.17 (m, 2H), 2.27 (m, 1H), 2.82 (t, 2H), 2.90 (td, 1H), 2.94 (t, 2H), 3.20 (q, 1H), 3.87 (s, 2H), 5.13 (br.), 6.65. (d, 1H), 6.80 (dd, 1H), 7.19 (d, 1H), 7.22 (m, 3H), 7.35 (d, 1H), 8.80 (br.s, 1H).

7-(N-tert-Butoxycarbonyl-3-chlorobenzylamino)ethyl-1,2,3,3a,5,9b-hexahydrocyclopenta[c]quinoline-4-thione A solution of 69 mg (0.19 mmol) of 7-(3-chlorobenzylamino)-ethyl-1,2,3,3a,5,9b-hexahydrocyclopenta[c]quinolin-4-one in 10 ml of dichloromethane is mixed with 46 mg (0.21 mmol) of di-tert-butylcarboxylic acid anhydride and 2 mg (0.02 mmol) of 4-(dimethylamino)pyridine. After 15 hours at room temperature, the batch is diluted with methyl-tert-butyl ether (100 ml), washed with 10% citric acid and saturated NaCl, dried (Na$_2$SO$_4$) and concentrated by evaporation in a vacuum. The residue is dissolved in 1,2-dimethoxyethane (10 ml) and treated with 202 mg (0.5 mmol) of Lawesson's reagent. After 6 hours at room temperature, the batch is concentrated by evaporation, and the residue is purified by column chromatography with hexane-ethyl acetate: 48 mg of product.

$^1$H-NMR (CDCl$_3$): 1.45 (s, 9H), 1.54–1.75 (m, 2H), 1.89 (m, 1H), 2.07–2.36 (m, 3H), 2.55 (br., 2H), 3.21–3.48 (m, 4H), 4.35 (br., 2H), 6.52 (br., 1H), 6.88 (br., 1H), 7.09 (br., 1H), 7.15 (d, 1H), 7.18 (m, 1H), 7.25 (m, 2H), 9.32 (s, 1H).

EXAMPLE 1

4-Amino-7-(N-tert-butoxycarbonyl-3-chlorobenzylamino)methyl-2,3,3a,9b-tetrahydro-1H-cyclopenta[c]quinoline 60 mg (0.13 mmol) of 7-(N-tert-butoxycarbonyl-3-chlorobenzylamino)methyl-1,2,3,3a,5,9b-hexahydrocyclopenta[c]quinoline-4-thione is suspended in 10 ml of 7 M ammoniacal methanol. After 15 hours at room temperature, the reaction solution is concentrated by evaporation, and the residue is purified by column chromatography on silica gel with dichloromethane-ethanol: 47 mg of product.

$^1$H-NMR (CDCl$_3$): 1.50 (s, 9H), 1.63–2.00 (m, 4H), 2.16 (m, 2H), 2.77 (q, 1H), 3.29 (q, 1H), 4.29 (br., 2H), 4.38 (br., 2H), 4.73 (br., 2H), 6.85 (br., 2H), 7.09 (d, 1H), 7.01–7.30 (m, 4H).

MS (FAB) m/e=440 (M$^+$)

EXAMPLE 2

4-Amino-7-(3-chlorobenzylamino)methyl-2,3,3a,9b-tetrahydro-1H-cyclopenta[c]quinoline Dihydrochloride 44 mg (0.10 mmol) of 4-amino-7-(N-tert-butoxycarbonyl-3-chlorobenzylamino)-methyl-2,3,3a,9b-tetrahydro-1H-cyclopenta[c]quinoline is stirred in 3 ml of 4 M hydrochloric acid dioxane for 2-hours at room temperature. After 1 ml of toluene is added, the solution is concentrated by evaporation to 1 ml and decanted. The residue is dissolved in 3 ml of methanol, and the solution is concentrated by evaporation. The residue is treated with 1 ml of chloroform, and the solvent is distilled off: 40 mg.

$^1$H-NMR (CD$_3$OD): 1.53–1.79 (m, 3H), 2.06 (m, 1H), 2.17–2.33 (m, 2H), 3.19 (q, 1H), 3.49 (m, 1H), 4.18 (s, 2H), 4.21 (s, 2H), 7.22 (s, 1H), 7.28 (d, 1H), 7.38 (s, 3H), 7.40 (d, 1H), 7.50 (s, 1H).

MS (FAB) m/e=340 ([M−2 HCl]$^+$)

EXAMPLE 3

4-Amino-7-(N-tert-butoxycarbonyl-3-chlorobenzylamino)ethyl-2,3,3a,9b-tetrahydro-1H-cyclopenta[c]quinoline 45 mg (0.096 mmol) of 7-(N-tert-butoxycarbonyl-3-chlorobenzylamino)ethyl-1,2,3,3a,5,9b-hexahydrocyclopenta[c]quinoline-4-thione is dissolved in 20 ml of 6 M ammoniacal methanol. After 15 hours at room temperature, the batch is concentrated by evaporation, and the residue is purified by column chromatography with dichloromethane-ethanol-33% NH$_4$OH: 25 mg of product.

$^1$H-NMR (CDCl$_3$): 1.38–1.55 (br., 9H), 1.60–1.95 (m, 4H), 2.07–2.22 (m, 2H), 2.66–2.82 (m, 3H), 3.22–3.48 (m, 3H), 4.03 (br., 2H), 4.25–4.40 (br., 2H), 6.70–6.85 (br., 2H), 7.04 (d, 1H), 7.08 (m, 1H), 7.15–7.24 (m, 3H).

MS (FAB) m/e=454 (M$^+$)

EXAMPLE 4

4-Amino-7-(3-chlorobenzylamino)ethyl-2,3,3a,9b-tetrahydro-1H-cyclopenta[c]quinoline Dihydrochloride 19 mg (0.042 mmol) of 4-amino-7-(N-tert-butoxycarbonyl-3-chlorobenzylamino)-ethyl-2,3,3a,9b-tetrahydro-1H-cyclopenta[c]quinoline is dissolved in 3 ml of 4 M hydrochloric acid dioxane. After 15 hours at room temperature, the reaction solution is concentrated by evaporation to 1 ml, and the solvent is decanted. The residue is suspended in chloroform and concentrated by evaporation: 17 mg of a glass-like solid.

$^1$H-NMR (CD$_3$OD): 1.60–1.88 (m, 3H), 2.10–2.42 (m, 3H), 3.06 (t, 2H), 3.24 (q, 1H), 3.31 (t, 0.2H), 3.53 (m, 1H), 4.28 (s, 2H), 7.08 (s, 1H), 7.17 (d, 1H), 7.38 (d, 1H), 7.48 (s, 3H), 7.61 (s, 1H).

MS (EI) m/e=353 ([M−2 HCl]$^+$)

EXAMPLE 5

4-Amino-7-[1-(N-tert-butoxycarbonyl-3-chlorobenzylamino)propyl]-2,3,3a,9b-tetrahydro-1H-cyclopenta[c]quinoline Starting Compounds 7-(Methoxycarbonylethenyll)-1,2,3,5-tetrahydrocyclopenta[c]quinolin-4-one A suspension of 528 mg (2.0 mmol) of 7-bromo-1,2,3,5-tetrahydrocyclopenta[c]quinolin-4-one, 0.36 ml of (4.0 mmol) of acrylic acid-methyl ester, 116 mg (0.1 mmol) of tetrakis(triphenylphosphine)palladium and 0.56 ml (4.0 mmol) of triethylamine in 25 ml of DMF is stirred for 3 hours at 120° C. The batch is diluted with ethyl acetate, washed with water, dried (Na$_2$SO$_4$) and concentrated by evaporation in a vacuum. Purification of the residue on silica gel with dichloromethane-ethanol yields 550 mg of product.

$^1$H-NMR ([D$_6$]-DMSO) δ=2.12 (pent, 2H), 2.80 (t, 2H), 3.12 (t, 2H), 3.77 (s, 3H), 6.61 (d, 1H), 7.52 (s, 1H), 7.56 (s, 2H), 7.67 (d, 1H), 11.19 (br.s, 1H).

7-(Methoxycarbonylethyl)-1,2,3,3a,5,9b-hexahydrocyclopenta[c]quinolin-4-one

A solution of 550 mg (2.0 mmol) of 7-(methoxycarbonylethyl)-1,2,3,5-tetrahydrocyclopenta[c]-quinolin-4-one in 130 ml of methanol-THF 3:1 is mixed with 972 mg (40.0 mmol) of magnesium and stirred for 24 hours at room temperature. The reaction mixture is filtered over glass fibers, the filter residue is washed with dichloromethane-methanol, and the combined filtrates are concentrated by evaporation in a vacuum. Purification of the residue on silica gel yields 120 mg of product.

$^1$H-NMR (CDCl$_3$): δ=1.57–1.77 (m, 3H), 2.02–2.18 (m, 2H), 2.31 (m, 1H), 2.63 (t, 2H), 2.91 (t, 2H), 2.94 (td, 1H), 3.23 (q, 1H), 3.69 (s, 3H), 6.58 (d, 1H), 6.84 (dd, 1H), 7.12 (d, 1H), 8.11 (br.s, 1H).

7-[1-(3-Chlorobenzylamino)propyl]-1,2,3,3a,5,9b-hexahydrocyclopenta[c]quinolin-4-one 1.6 ml (1.9 mmol) of 1.2 M diisobutylaluminum hydride (DIBAH) in toluene is added in drops to a solution of 510 mg (1.9 mmol) of 7-(methoxycarbonylethyl)-1,2,3,3a,5,9b-hexahydrocyclopenta[c]quinolin-4-one in 50 ml of toluene at −70° C. After 2 hours at −70° C., the batch is mixed with 0.75 ml (0.9 mmol) of DIBAH solution, stirred for 15 minutes, treated with 3 ml of isopropanol and 1 ml of water and stirred for 2 hours at room temperature. The reaction solution is filtered and concentrated by evaporation in a vacuum. The residue is dissolved in 50 ml of 1,2-dichloroethane, mixed with 0.38 ml (3.1 mmol) of 3-chlorobenzylamine, 0.91 g (4.3 mmol) of sodium (triacetoxy)-borohydride and 0.017 ml (0.29 mmol) of acetic acid and stirred for 24 hours at room temperature. The batch is diluted with ethyl acetate, washed with water, dried (Na$_2$SO$_4$) and concentrated by evaporation in a vacuum. Column chromatography on silica gel with ethyl acetate-methanol yields 290 mg of product.

MS (CI) m/e=369 (M$^+$)

7-[1-(N-tert-Butoxycarbonyl-3-chlorobenzylamino)propyl]-1,2,3,3a,5,9b-hexahydrocyclopenta[c]quinolin-4-one A solution of 290 mg (0.79 mmol) of 7-[1-(3-chlorobenzylamino)propyl]-1,2,3,3a,5,9b-hexahydrocyclopenta[c]quinolin-4-one in 20 ml of dichloromethane is mixed with 206 mg (0.94 mmol) of di-tert-butylcarboxylic acid anhydride and stirred for 24 hours at room temperature. The batch is diluted with dichloromethane, washed with water, dried (Na$_2$SO$_4$) and concentrated by evaporation in a vacuum. Column chromatography on silica gel with hexane-ethyl acetate yields 260 mg of product.

MS (FAB) m/e=469 (M$^+$)

7-[1-(N-tert-Butoxycarbonyl-3-chlorobenzylamino)propyl]-1,2,3,3a,5,9b-hexahydrocyclopenta[c]quinoline-4-thione A solution of 260 mg (0.55 mmol) of 7-[1-(N-tert-butoxycarbonyl-3-chlorobenzylamino)propyl]-1,2,3,3a,5,9b-hexahydrocyclopenta[c]quinolin-4-one and 597 mg (1.48 mmol) of Lawesson's reagent in 30 ml of THF is refluxed for 1 hour. After concentration by evaporation in a vacuum, the residue is purified by column chromatography with hexane-ethyl acetate: 230 mg of product.

MS (FAB) m/e=485 (M$^+$)

4-Amino-7-[1-(N-tert-butoxycarbonyl-3-chlorobenzylamino)propyl]-2,3,3a,9b-tetrahydro-1H-cyclopenta[c]quinoline 230 mg (0.47 mmol) of 7-[1-(N-tert-butoxycarbonyl-3-chlorobenzylamino)propyl]-1,2,3,3a,5,9b-hexahydrocyclopenta[c]quinoline-4-thione is stirred in 20 ml of 7 M ammoniacal methanol for 24 hours at room temperature. After the volatile components are distilled off in a vacuum, the residue is purified by column chromatography with dichloromethane-methanol on silica gel: 150 mg of product.

MS (FAB) m/e=468 (M$^+$)

EXAMPLE 6

4-Amino-7-[(1-(3-chlorobenzylamino)propyl]-2,3,3a,9b-tetrahydro-1H-cyclopenta[c]quinoline 150 mg (0.32 mmol) of 4-amino-7-[1-(N-tert-butoxycarbonyl-3-chlorobenzylamino)-propyl]-2,3,3a,9b-tetrahydro-1H-cyclopenta[c]quinoline is stirred in 5 ml of 4 M hydrochloric acid dioxane for 30 minutes at room temperature. The volatile components are removed in a vacuum: 140 mg.

$^1$H-NMR (D$_6$-DMSO): 1.53 (m, 3H), 1.67 (m, 2H), 1.91–2.05 (m, 3H), 2.12–2.25 (m, 2H), 2.64 (t, 2H), 2.90 (m, 2H), 3.20 (q, 1H), 3.43 (m, 1H), 4.15 (t, 2H), 6.94 (d, 1H), 7.03 (dd, 1H), 7.28 (d, 2H), 7.43–7.55 (m, 3H), 7.68 (s, 1H), 8.93 (s, 1H), 9.29 (br., 2H), 9.70 (s 1H).

MS (FAB) m/e=367 ([M−2 HCl]$^+$)

EXAMPLE 7

4-Amino-7-(N-tert-butoxycarbonyl-3-chlorobenzylamino)ethyl-8-chloro-2,3,3a,9b-tetrahydro-1H-cyclopenta[c]quinoline Starting Compounds 7-Acetoxyethyl-1,2,3,3a,5,9b-hexahydrocyclopenta[c]quinolin-4-one A solution of 560 mg (2.4 mmol) of 7-hydroxyethyl-1,2,3,3a,5,9b-hexahydrocyclopenta[c]quinolin-4-one in 10 ml of pyridine is stirred with 5 ml of acetic anhydride for 24 hours at room temperature. The batch is concentrated by evaporation in a vacuum and purified by column chromatography on silica gel with hexane-ethyl acetate: 500 mg of product.

$^1$H-NMR (CDCl$_3$): 1.59–1.81 (m, 3H), 2.02–2.19 (m, 2H), 2.07 (s, 3H), 2.32 (m, 1H), 2.91 (t, 2H), 2.96 (td, 1H), 3.25 (q, 1H), 4.28 (t, 2H), 6.62 (d, 1H), 6.87 (dd, 1H), 7.15 (d, 1H), 8.25 (br.s, 1H).

7-Acetoxyethyl-8-chloro-1,2,3,3a,5,9b-hexahydrocyclopenta[c]quinolin-4-one

A solution of 400 mg (1.5 mmol) of 7-acetoxyethyl-1,2,3,3a,5,9b-hexahydrocyclopenta[c]quinolin-4-one and 193 mg (1.5 mmol) of N-chlorosuccinimide in 40 ml of DMF is heated for 6 days to 100° C. The batch is poured onto ice water and extracted with ethyl acetate. The organic phase is washed with 10% sulfuric acid and water, dried (Na$_2$SO$_4$) and concentrated by evaporation in a vacuum. Column chromatography on silica gel with hexane-ethyl acetate yields 380 mg of product.

$^1$H-NMR (CDCl$_3$): 1.59–1.78 (m, 3H), 2.02–2.20 (m, 2H), 2.06 (s, 3H), 2.30 (m, 1H), 2.93 (td, 1H), 3.03 (t, 2H), 3.23 (q, 1H), 4.29 (t, 2H), 6.67 (s, 1H), 7.20 (s, 1H), 8.51 (br.s, 1H).

8-Chloro-7-hydroxyethyl-1,2,3,3a,5,9b-hexahydrocyclopenta[c]quinolin-4-one 380 mg (1.2 mmol) of 7-acetoxyethyl-8-chloro-1,2,3,3a,5,9b-hexahydrocyclopenta[c]quinolin-4-one is dissolved in 30 ml of methanol and mixed with 341 mg (2.5 mmol) of potassium carbonate. After 3 days at room temperature, the batch is diluted with ethyl acetate, washed with water, dried (Na$_2$SO$_4$) and concentrated by evaporation in a vacuum.

Column chromatography on silica gel with ethyl acetate-ethanol yields 270 mg of product.

$^1$H-NMR (D$_6$-DMSO/CDCl$_3$): 1.38–1.63 (m, 3H), 1.85 (m, 2H), 2.14 (m, 1H), 2.72 (td, 1H), 2.78 (t, 2H), 3.07 (q, 1H), 3.60 (q, 2H), 4.14 (t, 1H), 6.72 (s, 1H), 7.02 (s, 1H), 9.73 (s, 1H).

8-Chloro-7-(3-chlorobenzylamino)ethyl-1,2,3,3a,5,9b-hexahydrocyclopenta[c]quinolin-4-one 0.22 ml (3.12 mmol) of DMSO in 2 ml of 1,2-dichloroethane is added in drops to a solution of 0.18 ml (2.04 mmol) of oxalyl chloride in 4 ml of 1,2-dichloroethane at −70° C. After 10 minutes at −70° C., a solution of 270 mg (1.02 mmol) of 8-chloro-7-hydroxyethyl-1,2,3,3a,5,9b-hexahydrocyclopenta[c]quinolin-4-one in 5 ml of 1,2-dichloroethane and 2 ml of DMSO are added in drops to it. After 2 hours at −70° C., the batch is diluted with 30 ml of dichloromethane and stirred for 3 hours at −70° C. After 1.27 ml (9.18 mmol) of triethylamine is added, the reaction solution is stirred for 1 hour at room temperature and concentrated by evaporation in a vacuum. The residue is taken up in 20 ml of 1,2-dichloroethane and 20 ml of THF and mixed with 0.14 ml (1.53 mmol) of 3-chlorobenzylamine, 323 mg (1.53 mmol) of sodium (triacetoxy)borohydride and 0.6 ml (10.2 mmol) of acetic acid. After 24 hours at room temperature, the batch is diluted with ethyl acetate, washed with water, dried (Na$_2$SO$_4$) and concentrated by evaporation in a vacuum. Column chromatography on silica gel with dichloromethane-methanol yields 220 mg of product.

$^1$H-NMR (D$_6$-DMSO/CDCl$_3$): 1.33–1.66 (m, 3H), 1.99 (m, 2H), 2.08 (m, 1H), 2.76 (t, 2H), 2.96 (br., 2H), 3.12 (q, 1H), 4.25-4.36 (m, 4H), 5.72 (br., 1H), 7.07–7.23 (m, 5H), 7.16 (s, 1H), 7.40 (s, 1H), 9.89 (s, 1H).

7-(N-tert-Butoxycarbonyl-3-chlorobenzylamino)ethyl-8-chloro-1,2,3,3a 5,9b-hexahydrocyclopenta[c]quinolin-4-one A solution of 220 mg (0.57 mmol) of 8-chloro-7-(3-chlorobenzylamino)ethyl-1,2,3,3a,5,9b-hexahydrocyclopenta[c]quinolin-4-one in 20 ml of dichloromethane is mixed with 149 mg (0.68 mmol) of di-tert-butylcarboxylic acid anhydride. After 24 hours at room temperature, the batch is diluted with dichloromethane, washed with water, dried (Na$_2$SO$_4$) and concentrated by evaporation in a vacuum. Column chromatography on silica gel with hexane-ethyl acetate yields 90 mg of product.

MS (CI) m/e=489.

7-(N-tert-Butoxycarbonyl-3-chlorobenzylamino)ethyl-8-chloro-1,2,3,3a,5,9b-hexahydrocyclopenta[c]quinoline-4-thione A solution of 90 mg (0.18 mmol) of 7-(N-tert-butoxycarbonyl-3-chlorobenzyl-amino)ethyl-8-chloro-1,2,3,3a,5,9b-hexahydrocyclopenta[c]quinolin-4-one and 194 mg (0.48 mmol) of Lawesson's reagent are stirred for 1 hour at room temperature and refluxed for 1 hour. After concentration by evaporation in a vacuum, the residue is purified by column chromatography with hexane-ethyl acetate: 80 mg of product.

MS (CI) m/e=505.

4-Amino-7-(N-tert-butoxycarbonyl-3-chlorobenzylamino) ethyl-8-chloro-2,3,3a,9b-tetrahydro-1H-cyclopenta[c]quinoline 80 mg (0.16 mmol) of 7-(N-tert-butoxycarbonyl-3-chlorobenzylamino)ethyl-8-chloro-1,2,3,3a,5,9b-hexahydrocyclopenta[c]quinoline-4-thione is stirred in 20 ml of 7 M ammoniacal methanol for 24 hours at room temperature. The batch is concentrated by evaporation and purified by column chromatography with dichloromethane-methanol: 80 mg of product.

MS (CI) m/e=488 (M$^+$)

EXAMPLE 8

4-Amino-8-chloro-7-(3-chlorobenzylamino)ethyl-2,3,3a,9b-tetrahydro-1H-cyclopenta[c]quinoline Dihydrochloride 80 mg (0.16 mmol) of 4-amino-7-(N-tert-butoxycarbonyl-3-chlorobenzylamino)ethyl-8-chloro-2,3,3a,9b-tetrahydro-1H-cyclopenta[c]quinoline is stirred in 2.5 ml of 4 M hydrochloric acid dioxane for 30 minutes at room temperature. The volatile components are distilled off in a vacuum: 90 mg of residue.

MS (CI) m/e=388 ([MH$^+$−2 HCl])

EXAMPLE 9

4-Amino-7-(N-tert-butoxycarbonyl-3-chlorobenzylamino)-1,2,3,3a,7,8,9,10b-octahydro-dicyclopenta[c,g]quinoline Starting Compounds 8-(Methoxycarbonylethenyl)-1,2,3,3a,5,9b-hexahydrocyclopenta[c]quinolin-4-one A solution of 4.0 g (15.0 mmol) of 8-bromo-1,2,3,3a,5,9b-hexahydrocyclo-penta[c]quinolin-4-one (DE file number: 198 06 348.2) in 150 ml of DMF is heated for 4 hours to 120° C. with 2.7 ml (30.0 mmol) of acrylic acid-methyl ester, 4.2 ml (30 mmol) of triethylamine, 168 mg (0.75 mmol) of palladium(II) acetate and 457 mg (1.5 mmol) of tri-o-tolyl-phosphine. After 868 mg (0.75 mmol) of tetrakis (triphenylphosphine)palladium is added, the batch is stirred for 18 hours at 120° C., diluted at room temperature with ethyl acetate, washed with water, dried (Na$_2$SO$_4$) and concentrated by evaporation in a vacuum. Column chromatography on silica gel with hexane-ethyl acetate yields 2.05 g of product.

$^1$H-NMR (CDCl$_3$): δ=1.59–1.80 (m, 3H), 2.14 (m, 2H), 2.34 (m, 1H), 2.98 (td, 1H), 3.29 (q, 1H), 3.83 (s, 3H), 6.36 (d, 1H), 6.81 (d, 1H), 7.35 (dd, 1H), 7.38 (d, 1H), 7.64 (d, 1H), 8.64 (br.s, 1H).

8-(Methoxycarbonylethyl)-1,2,3,3a,5,9b-hexahydrocyclopenta[c]quinolin-4-one 2.73 g (10.1 mmol) of 8-(methoxycarbonylethenyl)-1,2,3,3a,5,9b-hexahydrocyclopenta[c]quinolin-4-one is dissolved in 100 ml of ethyl acetate, and after 273 mg of 10% Pd-C and 0.1 ml of acetic acid are added, it is stirred for 24 hours in a hydrogen atmosphere. After filtration, the filtrate is concentrated by evaporation and purified by column chromatography on silica gel with hexane-ethyl acetate: 2.7 g.

$^1$H-NMR (CDCl$_3$): δ=1.57–1.78 (m, 3H), 2.11 (m, 2H), 2.32 (m, 1H), 2.62 (t, 2H), 2.90 (t, 2H), 2.95 (td, 1H), 3.24 (q, 1H), 3.68 (s, 3H), 6.68 (d, 1H), 7.00 (dd, 1H), 7.04 (d, 1H), 8.11 (br.s, 1H).

8-(Carboxyethyl)-1,2,3,3a,5,9b-hexahydrocyclopenta[c]quinolin-4-one

A solution of 2.7 g (9.9 mmol) of 8-(methoxycarbonyl-ethyl)-1,2,3,3a,5,9b-hexahydrocyclopenta[c]quinolin-4-one in 30 ml of THF and 50 mL of methano is mixed with 19.8 ml (19.8 mmol) of 1M NaOH solution and stirred for 24 hours at room temperature. With 10% sulfuric acid, the batch is set at pH 5 and extracted with ethyl acetate. The combined extracts are washed with water, dried (Na₂SO₄) and concentrated by evaporation in a vacuum.

Column chromatography on silica gel with ethyl acetate-hexane yields 2.06 g of product.

¹H-NMR (D₆-DMSO) δ=1.45 (pent, 1H), 1.61 (m, 2H), 1.93 (m, 1H), 1.99 (m, 1H), 2.16 (m, 1H), 2.50 (t, 2H), 2.75 (t, 2H), 2.80 (td, 1H), 3.17 (q, 1H), 6.77 (d, 1H), 6.98 (dd, 1H), 7.06 (d, 1H), 9.91 (br., 1H), 12.00 (br., 1H).

1,2,3,3a,7,8,9,10b-Octahydro-dicyclopenta[c,g]quinoline-4,7-dione

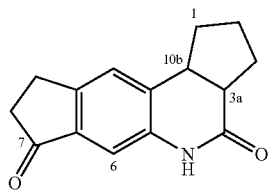

1.0 g (3.9 mmol) of 8-(carboxyethyl)-1,2,3,3a,5,9b-hexahydrocyclopenta[c]quinolin-4-one is added in portions to 16 g of polyphosphoric acid, which was heated beforehand to 120° C. After 1 hour at 120° C., the reaction solution is poured onto ice water and extracted with dichloromethane. The combined extracts are dried (Na₂SO₄) and concentrated by evaporation in a vacuum. Column chromatography of the residue on silica gel with hexane-ethyl acetate yields 400 mg of product.

¹H-NMR (CDCl₃): δ=1.59–1.83 (m, 3H), 2.12 (m, 2H), 2.42 (m, 1H), 2.70 (m, 2H), 2.98 (td, 1H), 3.09 (m, 2H), 3.31 (q, 1H), 7.15 (s, 1H), 7.32 (s, 1H), 8.44 (br.s, 1H).

1,2,3,3a,8,9,10c-Octahydro-dicyclopenta[c,f]quinoline-4,10-dione is produced as a by-product:

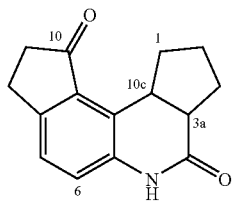

¹H-NMR (CDCl₃): δ=1.35 (m, 1H), 1.77 (m, 2H), 2.12 (m, 1H), 2.31 (m, 1H), 2.56 (m, 1H), 2.73 (m, 2H), 2.96 (td, 1H), 3.10 (m, 2H), 4.23 (dt, 1H), 7.03 (d, 1H), 7.28 (d, 1H), 8.95 (br.s, 1H).

7-(N-tert-Butoxycarbonyl-3-chlorobenzylamino)-1,2,3,3a,7,8,9,10b-octahydro-dicyclopenta[c,g]quinolin-4-one A solution of 400 mg (1.66 mmol) of 1,2,3,3a,7,8,9,10b-octahydro-dicyclo-penta[c,g]quinoline-4,7-dione in 50 ml of 1,2-dichloroethane and 50 ml of THF is mixed with 0.22 ml (1.82 mmol) of 3-chlorobenzylamine, 526 mg (2.49 mmol) of sodium (triacetoxy)borohydride and 0.01 ml (0.17 mmol) of acetic acid. After 24 hours at room temperature, 0.44 ml (3.6 mmol) of 3-chlorobenzylamine, 1.05 g (5.0 mmol) of sodium(triacetoxy)-borohydride and 0.02 ml (0.34 mmol) of acetic acid are added to it and stirred for another 24 hours at room temperature. The reaction solution is diluted with ethyl acetate, washed with water, dried (Na₂SO₄) and concentrated by evaporation in a vacuum.

Column chromatography on silica gel with hexane-ethyl acetate yields 360 mg of 7-(3-chlorobenzylamino)-1,2,3,3a,7,8,9,10b-octahydro-dicyclopenta[c,g]quinolin-4-one.

69 mg (0.32 mmol) of di-tert-butylcarboxylic acid anhydride is added to a solution of 140 mg (0.26 mmol) of 7-(3-chlorobenzylamino)-1,2,3,3a,7,8,9,10b-octahydro-dicyclopenta[c,g]quinolin-4-one in 20 ml of dichloromethane. After 24 hours, another 17 mg (0.08 mmol) of di-tert-butylcarboxylic acid anhydride is added, the batch is stirred for 24 hours at room temperature, diluted with dichloromethane, washed with water, dried (Na₂SO₄) and concentrated by evaporation in a vacuum. Column chromatography on silica gel with hexane-ethyl acetate yields 60 mg of product.

MS (FAB) m/e=467 (M⁺).

7-(N-tert-Butoxycarbonyl-3-chlorobenzylamino)-1,2,3,3a,7,8,9,10b-octahydrodicyclopenta[c,g]quinoline-4-thione A solution of 100 mg (0.21 mmol) of 7-(N-tert-butoxycarbonyl-3-chlorobenzyl-amino)-1,2,3,3a,7,8,9,10b-octahydro-dicyclopenta[c,g]quinolin-4-one and 96 mg (0.23 mmol) of Lawesson's reagent in 10 ml of DME is stirred for 2 hours at room temperature. After concentration by evaporation, the residue is purified by column chromatography on silica gel with hexane-ethyl acetate: 70 mg of product.

MS (FAB) m/e=483 (M⁺).

4-Amino-7-(N-tert-butoxycarbonyl-3-chlorobenzylamino)-1,2,3,3a,7,8,9,10b-octahydro-dicyclopenta[c,g]quinoline 70 mg (0.15 mmol) of 7-(N-tert-butoxycarbonyl-3-chlorobenzylamino)-1,2,3,3a,7,8,9,10b-octahydro-dicyclopenta[c,g]quinoline-4-thione is dissolved in 15 ml of 7 M ammoniacal methanol and stirred for 40 hours at room temperature and for 16 hours at 40° C. After concentration by evaporation, the residue is purified by column chromatography on silica gel with dichloromethane-methanol-ammonia: 60 mg of product.

MS (ESI) m/e=466 (M

EXAMPLE 10

4-(Amino-7-(3-chlorobenzylamino)-1,2,3,3a,7,8,9,10b-octahydro-dicyclopenta[c,g]quinoline Dihydrochloride

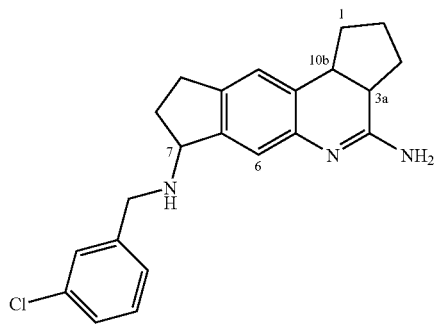

60 mg (0.13 mmol) of 4-amino-7-(N-tert-butoxycarbonyl-3-chlorobenzylamino)-1,2,3,3a,7,8,9,10b-octahydro-dicyclopenta[c,g]quinoline is stirred in 2 ml of 4 M hydrochloric acid dioxane for 30 minutes at room temperature. The volatile components are distilled off in a vacuum: 60 mg of residue.

MS (ESI) m/e=366 (M⁺–2 HCl).

The invention claimed is:

1. A compound of formula I,

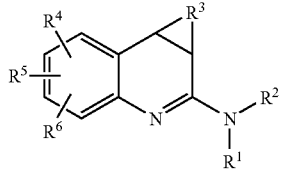

(I)

wherein
R¹ and R² are, independently of one another, hydrogen, $C_{1-6}$ alkyl, $OR^7$, $NR^7R^8$, CN, acyl, $CO_2R^9$, $CONR^7R^8$ or $CSNR^7R^8$,
R³ is a saturated or unsaturated $C_{1-5}$ alkylene radical, which is optionally substituted in 1 to 4 places with $OR^7$, $NR^{11}R^{12}$ or $C_{1-4}$ alkyl and which is optionally bridged with a methano, ethano or propano group
R⁴ is $C_{1-4}$ alkyl substituted with $NR^{14}R^{15}$,
R⁵ is hydrogen, halogen, $OR^7$, $C_{1-4}$ alkyl, $CF_3$, or $OCF_3$, or, R⁴ and R⁵ optionally together with 2 adjacent carbon atoms form a $C_3$–$C_4$ alkylene moiety optionally substituted in one or two places with $NR^{14}R^{15}$,
R⁶ is Hydrogen, halogen, $OR^7$, $C_{1-4}$ alkyl, $CF_3$, or $OCF_3$,
R⁷, R¹⁸ and R¹⁹ are, independently of one another, Hydrogen, $C_{1-4}$ alkyl or $C_{6-10}$ aryl, which optionally is substituted with halogen or $C_{1-4}$ alkyl,
R⁸, R¹¹ and R¹² are, independently of one another, Hydrogen, $C_{1-6}$ alkyl or $C_{6-10}$ aryl, which optionally is substituted with halogen or $C_{1-4}$ alkyl, $COR^{10}$, $CO_2R^{10}$, $CONR^{18}R^{19}$ or $CSNR^{18}R^{19}$,
R⁹, R¹⁰ and R²⁰ are, independently of one another, $C_{1-6}$ alkyl or $C_{6-10}$ aryl, which optionally is substituted with halogen or $C_{1-4}$ alkyl,
R¹⁴ and R¹⁵ are, independently of one another, Hydrogen, $CO_2R^{20}$ or $C_{1-6}$ alkyl, which optionally is substituted with halogen, hydroxy, $C_{1-4}$ alkoxy, nitro, amino, $C_{1-6}$ alkyl, trifluoromethyl, carboxyl, cyano, carboxamido, $C_{3-7}$ cycloalkyl, indanyl, 1,2,3,4-tetrahydronaphthyl, $C_{6-10}$ aryl, wherein the aryl radical is optionally substituted with halogen, hydroxy, $C_{1-4}$ alkoxy, $C_{1-4}$ alkyl, $CF_3$, $NO_2$, $NH_2$, $N(C_{1-4}$ alkyl$)_2$ or carboxyl, and
n is 0, 1 or 2,
or a tautomeric or isomeric form of or a salt of a compound of formula I.

2. A compound according to claim 1, in which R³ is a $C_{1-5}$ alkylene radical, which is optionally bridged with a methano, ethano or propano group.

3. A compound according to claim 1, in which R¹ and R² is hydrogen.

4. A pharmaceutical composition comprising an effective amount of a compound according to claim 1, and a pharmaceutically acceptable vehicle or adjuvant.

5. A compound of formula I,

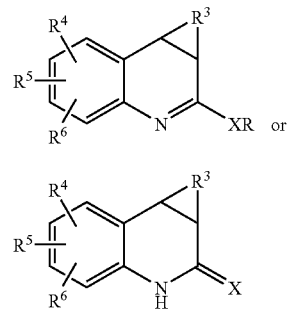

wherein
R¹ and R² are, each independently, hydrogen or $C_{1-6}$ alkyl,
R³ is a saturated or unsaturated $C_{1-5}$ alkylene radical, which is optionally substituted in 1 to 4 places with $OR^7$, $NR^{11}R^{12}$ or $C_{1-4}$ alkyl and which is optionally bridged with a methano, ethano or propano group,
R⁴ is $C_{1-4}$ alkyl, substituted with $NR^{14}R^{15}$,
R⁵ is hydrogen, halogen, $OR^7$, $C_{1-4}$ alkyl, $CF_3$, or $OCF_3$, or, R⁴ and R⁵ optionally together with 2 adjacent carbon atoms form a $C_3$–$C_4$ alkylene moiety optionally substituted in one or two places with $NR^{14}R^{15}$,
R⁶ is Hydrogen, halogen, $OR^7$, $C_{1-4}$ alkyl, $CF_3$, or $OCF_3$,
R⁷, R¹⁸ and R¹⁹ are, independently of one another, Hydrogen, $C_{1-6}$ alkyl or $C_{6-10}$ aryl, which optionally is substituted with halogen or $C_{1-4}$ alkyl,
R⁸, R¹¹ and R¹² are, independently of one another, Hydrogen, $C_{1-6}$ alkyl or $C_{6-10}$ aryl, which optionally is substituted with halogen or $C_{1-4}$ alkyl, $COR^{10}$, $CO_2R^{10}$, $CONR^{18}R^{19}$ or $CSNR^{18}R^{19}$,
R⁹, R¹⁰ and R²⁰ are, independently of one another, $C_{1-6}$ alkyl or $C_{6-10}$ aryl, which optionally is substituted with halogen or $C_{1-4}$ alkyl,
R¹⁴ and R¹⁵ are, independently of one another, Hydrogen, $CO_2R^{20}$ or $C_{1-6}$ alkyl, which optionally is substituted with halogen, hydroxy, $C_{1-4}$ alkoxy, nitro, amino, $C_{1-6}$ alkyl, trifluoromethyl, carboxyl, cyano, carboxamido, $C_{3-7}$ cycloalkyl, indanyl, 1,2,3,4-tetrahydronaphthyl, $C_{6-10}$ aryl, wherein the aryl radical is optionally substituted with halogen, hydroxy, $C_{1-4}$ alkoxy, $C_{1-4}$ alkyl, $CF_3$, $NO_2$, $NH_2$, $N(C_{1-4}$ alkyl$)_2$ or carboxyl, and
n is 0, 1 or 2,
or a tautomeric or isomeric form of or a salt of a compound of formula I.

6. A compound according to claim 5, wherein R³ is a $C_{1-5}$ alkylene radical, which is optionally bridged with a methano, ethano or propane group.

7. A compound according to claim 1, which is selected from the group consisting of:
4-amino-7-(N-tert-butyloxycarbonyl-3-chlorabenzylamino)methyl-2,3,3a,9b-tetrahydro-1H-cyclopenta[c]quinoline,
4-amino-7-(3-chlorobenzylamino)methyl-2,3,3a,9b-tetrahydro-1H-cyclopenta[c]quinoline dihydrochloride,
4-amino-7-(N-tert-butyloxycarbonyl-3-chlorobenzylamino)ethyl-2,3,3a,9b-tetrahydro-1H-cyclopenta[c]quinoline, 4-amino-7-(3-chlorobenzylamino)ethyl-2,3,3a,9b-tetrahydro-1H-cyclopenta[c]quinoline dihydrochloride, 4-amino-7-[1-(N-tert-butyloxycarbonyl-3-chlorobenzylamino)propyl]-2,3,3a,9b-tetrahydro-1H-cyclopenta[c]quinoline, 4-amino-7-[1-(3-chlorobenzylamino)propyl]-2,3,3a,9b-tetrahydro-1H-cyclopenta[c]quinoline dihydrochloride, 4-amino-7-(N-tert-butyloxycarbonyl-3-chlorobenzylamino)ethyl-8-chloro-2,3,3a,9b-tetrahydro-1H-cyclopenta[c]quinoline, 4-amino-8-chloro-7-(3-chlorobenzylamino)ethyl-2,3,3a,9b-tetrahydro-1 H-cyclopenta[c]quinoline dihydrochloride, 4-amino-7-(N-tert-butyloxycarbonyl-3-chlorobenzylamino)-1,2,3,3a,7,8,9,10b-octahydro-dicyclopenta[c,g]quinoline, and 4-amino-7-(3-chlorobenzylamino)methyl-1,2,3,3a,7,8,9,10b-octahydro-dicyclopenta[c,g]quinoline dihydrochloride.

8. A pharmaceutical composition according to claim 4, in which $R^3$ is a $C_{1-5}$ alkylene radical, which is optionally bridged with a methano, ethano or propano group.

9. A pharmaceutical composition according to claim 4, in which $R^1$ and $R^2$ is hydrogen.

10. A pharmaceutical composition according to claim 4, wherein the compound is selected from the group consisting of:

4-amino-7-(N-tert-butyloxycarbonyl-3-chlorobenzylamino)methyl-2,3,3a,9b-tetrahydro-1H-cyclopenta[c]quinoline, 4-amino-7-(3-chlorobenzylamino)methyl-2,3,3a,9b-tetrahydro-1H-cyclopenta[c]quinoline dihydrochloride, 4-amino-7-(N-tert-butyloxycarbonyl-3-chlorobenzylamino)ethyl-2,3,3a,9b-tetrahydro-1H-cyclopenta[c]quinoline, 4-amino-7-(3-chlorobenzylamino)ethyl-2,3,3a,9b-tetrahydro-1H-cyclopenta[c]quinoline dihydrochloride, 4-amino-7-[(1-(N-tert-butyloxycarbonyl-3-chlorobenzylamino)propyl]-2,3 ,3a,9b-tetrahydro-1H-cyclopenta[c]quinoline, 4-amino-7-[1-(3-chlorobenzylamino)propyl])-2,3,3a,9b-tetrahydro-1H-cyclopenta[c]quinoline dihydrochloride, 4-amino-7-(N-tert-butyloxycarbonyl-3-chlorobenzylamino)ethyl-8-chloro-2,3,3a,9b-tetrahydro-1H-cyclopenta[c]quinoline, 4-amino-8-chloro-7-(3-chlorobenzylamino)ethyl-2,3,3a,9b-tetrahydro-1H-cyclopenta[c]quinoline dihydrochloride, 4-amino-7-(N-tert-butyloxycarbonyl-3-chlorobenzylamino)-1,2,3, 3a,7,8,9,10b-octahydro-dicyclopenta[c,g]quinoline, and 4-amino-7-(3-chlorobenzylamino)methyl-1,2,3,3a,7,8,9,10b-octahydro-dicyclopenta[c,g]quinoline dihydrochloride.

* * * * *